United States Patent [19]

Chiu et al.

[11] Patent Number: 5,179,113

[45] Date of Patent: Jan. 12, 1993

[54] TREATMENT OF CENTRAL NERVOUS DISORDERS WITH IMIDAZOLE COMPOUNDS

[75] Inventors: Andrew T. Chiu, Landenberg, Pa.; Victor J. De Noble, Newark, Del.; John J. V. Duncia; Pancras C. B. Wong, both of Wilmington, Del.

[73] Assignee: E. I. Du Pont de Nemours and Company, Wilmington, Del.

[21] Appl. No.: 797,599

[22] Filed: Nov. 25, 1991

Related U.S. Application Data

[63] Continuation-in-part of Ser. No. 497,068, Mar. 20, 1990, abandoned.

[51] Int. Cl.$^5$ .................. A61K 31/41; A61K 31/415; A61K 31/44
[52] U.S. Cl. ................................... 514/382; 514/396; 514/399; 514/400; 514/303; 514/381; 514/398
[58] Field of Search ............... 514/303, 399, 381, 382

[56] References Cited

U.S. PATENT DOCUMENTS

| | | | |
|---|---|---|---|
| 4,301,169 | 11/1981 | Yamanaka | 424/273 R |
| 4,402,996 | 9/1983 | Yamanaka et al. | 424/273 R |
| 4,533,669 | 8/1985 | Yamanaka et al. | 514/396 |
| 4,602,031 | 7/1986 | Yamanaka et al. | 514/399 |
| 4,916,129 | 4/1990 | Carini et al. | 514/235.2 |

FOREIGN PATENT DOCUMENTS

| | | |
|---|---|---|
| 22279 | 3/1989 | Australia . |
| 288907 | 11/1988 | European Pat. Off. . |
| 307872 | 3/1989 | European Pat. Off. . |

OTHER PUBLICATIONS

Mann, Exp. Brain Res., vol. 4, suppl. pp. 242, 1982.
Fitzsimons, Rev. Physiol. Biochem, Pharmacol., vol. 87, pp. 117, 1980.
Scholken et al., Experientia., vol. 38, pp. 469, 1982.
Koller, et al., Neuroscience Lett., vol. 14, pp. 71-75, 1975.
Morgan and Routtengerg, Science, vol. 196, pp. 87-89, 1977.
Arregui, et al., J. Neurochem, vol. 38, pp. 1490-1692, 1982.
Zubenko, et al., Biol. Psych., vol. 21, pp. 1365-1381, 1986.
Usinger, et al., Drug. Dev. Research, vol. 14, pp. 315-324, 1988.
Costall, et al., Pharmacol, Biochem. Behav., vol. 33, pp. 573-579, 1989.
Barnes, et al., Brain Research, vol. 491, pp. 136-143, 1989.
Chiu et al., Biochem and Biophys. Res. Comm., vol. 165, pp. 196-203, 1989.
Whitebread et al, Biochem and Biophys. Res. Comm., vol. 163, pp. 284-291.
Bennet and Snyder, J. Biol. Chem., vol. 254, pp. 7423-7430, 1976.
Unger et al., Circulation, vol. 77 (suppl. I), pp. 40-54 (1988).

Primary Examiner—Frederick E. Waddell
Assistant Examiner—T. J. Criares

[57] ABSTRACT

Imidazole compounds such as 5-[4-(3-(N-isopropylamino)hydroxypropoxy)indole-2-carboxamidomethyl]-2-n-butyl-1-[(2'-carboxybiphenyl-4-yl)methyl]-4-chloroimidazole and their pharmaceutically suitable salts are useful for treating central nervous system disorders, such as cognitive and learning disorders, mediated by angiotensin-II.

4 Claims, No Drawings

TREATMENT OF CENTRAL NERVOUS DISORDERS WITH IMIDAZOLE COMPOUNDS

CROSS-REFERENCE TO RELATED APPLICATION

This application is a continuation-in-part of U.S. application Ser. No. 07/497,068, filed Mar. 20, 1990, now abandoned.

BACKGROUND OF THE INVENTION

Angiotensin-II (AII), in addition to being a circulating hormone, is now thought to act as a neuropeptide in the central nervous system (CNS) and may play a modulatory function on the release and subsequent action of other neurotransmitters (Unger et al. (1988) *Circulation* 77 (suppl I):40-54). Specific receptors for AII with high affinity have been identified and localized in different regions of the CNS (Mann (1982) *Esp. Brain Res.* 4 (suppl):242). Stimulation of AII receptors in the CNS elicits a complex but very reproducible and concerted pattern of behavioral, cardiovascular, and endocrine responses (Fitzsimons (1980) *Rev. Physiol. Biochem. Pharmacol* 87:117). These include CNS-induced elevation of blood pressure, increased drinking and sodium appetite, release of antidiuretic hormone, oxytocin, luteinizing hormone, and prolactin, and other effects (Scholken et al. (1982) *Experientia* 38:469). The CNS effects of AII could lead to hypertension and other cardiovascular diseases through inhibition of the baroreceptor reflex, increase in salt consumption, volume expansion, and increased peripheral resistance. Besides the cardiovascular system, AII may also influence the reproductive system and other brain functions, such as memory (Koller et al. (1975) *Neuroscience Lett.* 14:71-75).

The major functions of AII in the CNS can be classified into three groups which may share, at least in part, overlapping mechanisms of action. The first major function of AII in the CNS is regulation of body fluid volume in response to hypovolemia, involving, for example, regulation of thirst, blood pressure increases, vasopressin release, sodium appetite increase, adrenocorticotropic hormone (ACTH) release, and aldosterone release (Unger et al. (1988) *circulation* 77 (suppl I):-40-54, and references cited therein). This CNS function of AII is closely related to the role of AII in hypertension.

A second function of AII in the CNS, although poorly defined, is the regulation of gonadotrophic hormone releasing hormones and pituitary hormones during the reproductive cycle and pregnancy (Unger et al., supra).

A third possible CNS function of AII is a synaptic function. AII appears to interact with neurotransmitters such as acetylcholine (ACh), catecholamines, serotonin, and other peptides (Unger et al., supra). The amount of data supporting this CNS function of AII is limited. Published results suggest that increased AII activity in brain maintains an inhibitory control on cholinergic neurons resulting in impaired cognitive performance.

The role of peptides in learning and memory was initially investigated by DeWied in the late 1960's and early 1970's, and led Morgan and Routtenberg (*Science* (1977) 196:87-89) to investigate the role of AII in mediating retention of a passive avoidance (PA) response in rats. These authors demonstrated that rats injected with AII into the dorsal neostriatum, a brain area that has a high concentration of AII as well as precursors and metabolic enzymes for AII biosynthesis, showed a disruption in retention of a PA response. The authors demonstrated specificity of the response in terms of both the location in the brain and the peptide used (thyrotropin releasing hormone or lysine-8-vasopressin had no effect). This study showed that increased AII in the dorsal neostriatum results in a cognitive impairment which is most likely a result of AII modulation of neuronal activity that is necessary for consolidation of newly acquired information.

A different approach for investigating the behavioral effects of AII in the CNS was taken by Koller et al. (1975) *Neuroscience Letters* 14:71-75. These authors injected renin into the lateral ventricle of the brain (IVT) and measured increases in AII in cerebrospinal fluid (CSF); AII increased from 40 to about 5000 fmol per mL. This increase in AII was accompanied by a disruption of avoidance learning. These results suggested that renin-stimulated biosynthesis of AII could disrupt memory. IVT administration of the angiotensin-converting enzyme (ACE) inhibitors SQ 14225 (captopril), prior to the renin injection, prevented the renin-induced avoidance disruption. We have also shown in our laboratory that renin administered IVT produces a dose-related amnesia in a PA task, which is prevented by IVT administration of the ACE inhibitor captopril. These results suggest that increased AII levels in brain leads to a disruption of avoidance performance. Thus, this amnesia can be achieved by direct application into a discrete brain area of AII or renin, a stimulator of endogenous AII biosynthesis.

In the literature on the neuropathology and neurochemistry of Alzheimer's disease (AD) using human CSF and brain tissue, two reports of altered levels of dipeptidyl carboxypeptidase (angiotensin-converting enzyme, ACE) were published. Arrequi et al. (1982) *J. Neurochemistry* 38:1490-1492 found increased ACE activity in the hippocampus, parahippocampal gyrus, frontal cortex, and caudate nucleus in AD patients. Zubenko et al. (1986) *Biol. Psych.* 21:1365-1381, found a correlation between the severity of AD with levels of ACE in CSF. Whether the alterations in ACE are causative in the progression of dementia or correlates of the disease progress is not known.

Recent evidence that inhibition of ACE can have a modulatory effect on learning and memory was reported by Usinger et al. (1988) *Drug Dev. Research* 14:315-324 (also European Patent Application EP 307,872 to Hoechst, published 3/22/89). These authors investigated the effects of the ACE inhibitor Hoe 288 on:uphill avoidance in mice, scopolamine-induced (muscarinic receptor blocker) amnesia of a PA response, and a scopolamine-induced impairment of eight arm radial maze performance in rats. In the uphill avoidance test, an acute administration of Hoe 288 at 30 mg/kg PO improved performance during retention testing. In the scopolamine-induced PA amnesia, administration of Hoe 288 three times per day at 1, 3 and 10 mg/kg PO, partially reversed the amnesia. Finally, 3 mg/kg IP partially antagonized the effects of muscarinic receptor blockade on performance. Further, these authors demonstrated that acute or repeated administration of the ACE inhibitor induced a significant decrease in ACh in the striatum and hypothalamus.

Similar results were reported by Costall et al. (1989) *Pharmacol. Biochem. Behav.* 33:573-579, using the ACE inhibitor captopril. These authors demonstrated that the subchronic treatment with captopril increased the rate of acquisition of light/dark habituation performance. Further, anticholinergic scopolamine-induced disruption of performance in this test model was prevented by daily treatment with captopril.

The ACE inhibitor SQ 29852 has also been reported to provide protective effects on memory of previously learned tasks and to ameliorate, at least in part, an anticholinergic effect on performance (European Patent Application EP 288,907 to Squibb, published 11/2/88).

Evidence for a role of AII on cholinergic function was also reported by Barnes et al. (1989) *Brain Research* 491:136–143, who examined the affect of AII on an in vitro model of potassium stimulated release of [3H]ACh. AII, but not AI, reduced potassium-stimulated release of ACh without effects on basal levels. This effect was antagonized by the AII antagonist [1-sarcosine, 8-threonine]angiotensin-II. These results suggest that AII can inhibit the release of ACh in entorhinal cortex from rat brain.

The results summarized above suggest that increased AII activity in brain may maintain inhibitory control of cholinergic neurons, resulting in impaired cognitive performance.

SUMMARY OF THE INVENTION

According to the present invention there is provided a method of treating central nervous system (CNS) disorders, such as cognitive and learning disorders, mediated by AII in a mammal comprising administering to the mammal an effective amount of a compound having the formula (I):

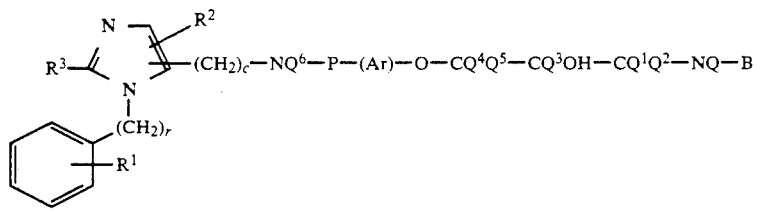

wherein
Q and $Q^1$–$Q^6$ are independently selected from hydrogen and alkyl of 1–4 carbon atoms;
P is a carbonyl group or

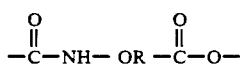

with N and O respectively, bonded to Ar;
B is an alkyl group of 1 to 6 carbon atoms;
Any of the —(CH$_2$)$_c$— groups independently are optionally substituted by one or two alkyl groups of 1 to 4 carbon atoms;
Ar is a benzene ring or a naphthyl or indolyl ring system any of which is optionally substituted in any position by one or more substituents independently selected from alkyl groups of 1 to 4 carbon atoms being optionally substituted by one or more halogen atoms, alkoxy of 1 to 9 carbon atoms, halogen, nitro, amino, carboxy, alkoxycarbonyl of 1 to 4 carbon atoms, and hydroxy;
$R^1$ is —4—COOH; —4—CO$_2R^7$;

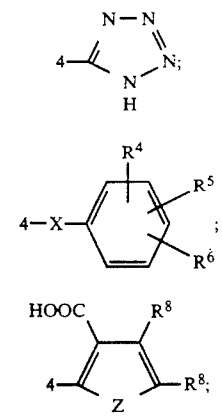

NHSO$_2$CF$_3$; CONHOR$^9$.

$R^2$ is H, F, Cl, Br, I, NO$_2$, alkyl of 1 to 6 carbon atoms, perfluoroalkyl of 1 to 6 carbon atoms, phenyl, pentafluorophenyl, CN, COR$^{16}$;

$R^3$ is alkyl of 2 to 10 carbon atoms, alkenyl or alkynyl of 3 to 10 carbon atoms, alkylthio of 2 to 10 carbon atoms;

$R^4$ is H; Cl; Br; F; NO$_2$; alkyl of 1 to 4 carbon atoms; acyloxy of 1 to 4 carbon atoms; alkoxy of 1 to 4 carbon atoms; CO$_2$H; CO$_2R^7$; NHSO$_2$CH$_3$; NHSO$_2$CF$_3$; CONHOR$^9$; SO$_2$NH$_2$; aryl or furyl;

$R^5$ is H; Cl; Br; I or F; alkyl of 1 to 4 carbon atoms or alkoxy of 1 to 4 carbon atoms;

$R^6$ is —CO$_2$H; —CO$_2R^7$; —CH$_2$CO$_2$H; —CH$_2$CO$_2R^7$;

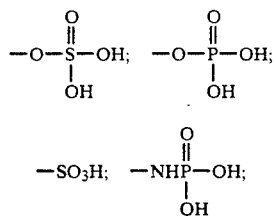

—PO$_3$H; —C(CF$_3$)$_2$OH; —NHSO$_2$CH$_3$; —NHSO$_2$CF$_3$; —NHCOCF$_3$; —CONHOR$^9$; —SO$_2$NH$_2$;

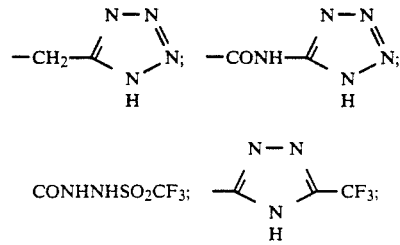

-continued $$\text{—} \overset{N=N}{\underset{R^{15}}{\diagdown}} NH; \text{ or } \text{—} \overset{N-N}{\underset{N}{\diagdown}} \overset{\diagdown}{\underset{H}{N}}$$

$R^7$ is $-\overset{R^{14}}{\underset{|}{CH}}-\overset{O}{\underset{||}{O}}CR^{11}$;

$R^8$ is H, alkyl of 1 to 6 carbon atoms, cycloalkyl of 3 to 6 carbon atoms, phenyl or benzyl;
$R^9$ is H, methyl or benzyl;
$R^{11}$ is alkyl of 1 to 6 carbon atoms; $-NR^{12}R^{13}$; or $$-\underset{NH_2}{\underset{|}{CHCH_2CO_2CH_3}}$$

$R^{12}$ and $R^{13}$ are independently H, alkyl of 1 to 6 carbon atoms, benzyl, or are taken together as $(CH_2)_u$, where u is 3 to 6;
$R^{14}$ is H, $CH_3$ or $-C_6H_5$;
$R^{15}$ = CN, $NO_2$ or $CO_2R^8$;
$R^{16}$ is H; alkyl of 1 to 6 carbon atoms; phenyl; phenylalkyl where alkyl is 1 to 6 carbon atoms; OH; alkoxy of 1 to 6 carbon atoms; phenoxy; benzyloxy; $NH_2$; alkylamino or dialkylamino where alkyl is 1 to 6 carbon atoms; or morpholino;
X is a carbon-carbon single bond, $-CO-$, $-O-$, $-S-$, $-NH-$, $-NHCO-$, $-CONH-$, $-OCH_2$, $-CH_2O-$, $-CH=CH-$, $-SCH_2-$, $-NHCH_2-$, $-CH_2-$, $-CH_2S-$, $-CH_2NH-$;
Z = O, S;
c = 1 to 10;
r = 0 to 2;
and pharmaceutically acceptable salts of these compounds.

Preferred in the method of this invention are compounds having the formula (II):

(II)

wherein
Q, $Q^1$–$Q^6$, P, B, Ar, and c are all defined as previously given for formula (I) and where
$R^2$ is H, Cl, Br, or I, alkyl of 1 to 4 carbon atoms, perfluoroalkyl of 1 to 3 carbon atoms, phenyl or $COR^{16}$ where $R^{16}$ is as previously given;
$R^3$ is alkyl, alkenyl or alkynyl of 3 to 7 carbon atoms;
$R^5$ is H, Cl, Br, I, or F, alkyl of 1 to 4 carbon atoms or alkoxy of 1 to 4 carbon atoms;
$R^6$ is $-CO_2H$, $NHSO_2CF_3$ or $$\text{—} \overset{N-N}{\underset{N}{\diagdown}} \overset{\diagdown}{\underset{H}{N}};$$

and their pharmaceutically acceptable salts.
More preferred in the method of the invention are compounds of formula (II) wherein
$R^5$ is H and $$R^6 \text{ is } -CO_2H \text{ or } \text{—} \overset{N-N}{\underset{N}{\diagdown}} \overset{\diagdown}{\underset{H}{N}}$$

and their pharmaceutically acceptable salts.

Two compounds illustrative of this more preferred scope of compounds are 5-[4-(3-(N-isopropylamino)hydroxypropoxy)indole-2-carboxamidomethyl]-2-n-butyl-1-[(2'-carboxybiphenyl-4-yl)methyl]-4-chloroimidazole and 4-[4-(3-N-isopropylamino)hydroxypropoxy)indole-2-carboxamidomethyl]-2-n-butyl-1-[(2'-(-1H-tetrazol-5-yl)biphenyl-4-yl)methyl]-5-carboxyimidazole.

When Ar represents a benzene ring, the P group can be attached at the ortho, meta or para position relative to the amino(hydroxy) alkoxy moiety. When Ar represents an indolyl ring system, most preferably the amino(hydroxy) alkoxy moiety is attached in the 4 or 5 position and the P group is in the 2 or 3 position. When Ar represents a naphthalene ring system, the amino(hydroxy) alkoxy moiety is preferably in the 1 or 2 position and the P group is in the 6 or 7 position.

Within the scope of this invention are methods of using pharmaceutical compositions comprising a suitable pharmaceutical carrier and a compound of formula (I) or formula (II) to treat CNS disorders, including memory and learning disfunction.

DETAILED DESCRIPTION OF THE INVENTION

The compounds of formula (I) and formula (II) useful in this invention are described in and prepared by methods set forth in copending, commonly assigned U.S. patent application U.S. Ser. No. 07/299,709, filed Jun. 19, 1989, allowed Sep. 26, 1989 (E. I. du Pont de Nemours & Co., Case BP-6393), page 6, line 14 through page 30, line 10, the disclosure of which is incorporated herein by reference.

Two distinct angiotensin-II (AII) receptor subtypes have been discovered and characterized by means of the discriminatory effect of dithiothreitol (DTT) and by two structurally dissimilar nonpeptide AII receptor antagonists, denoted as DuP 753 and EXP655, which show reciprocal selectivity for the two subtypes (Chiu et al., *Biochem. and Biophys. Res. Comm.* (1989) 165:196-203). DuP 753 is 2-n-butyl-4-chloro-5-hydroxymethyl-1-[(2'-(1H-tetrazol-5-yl)biphenyl-4-yl)methyl]-imidazole (Example 89 of European Published Application EPA 0 324 377). EXP655 (PD 123,177) is 1-(4-amino-3-methylphenyl)methyl-5-diphenylacetyl-4,5,6,7-tetrahydro-1H-imidazo[4,5-c]pyridine-6-carboxylic acid (Example 13 of EPA 0 245 637).

Using radioligand-receptor binding techniques, DuP 753 was found to be highly specific for an AII receptor site, designated AII receptor subtype-1 or AII-1, displaying an inhibitory constant $IC_{50}$ value of about $1.2 \times 10^{-8}M$ in rat adrenal cortex. This type of AII receptor was particularly sensitive to inactivation by DTT. EXP655 exhibited very low affinity for the AII-1 site ($IC_{50}$ value of about $3.0 \times 10^{-4}M$), but was highly selective for a distinct AII receptor site, designated AII receptor subtype-2 or AII-2, exhibiting an inhibitory constant $IC_{50}$ value of about $1.0 \times 10^{-7}M$ in rat adrenal cortex. In contrast to the AII-1 receptor, the AII-2 receptor was resistant to DTT inactivation. Moreover, DuP 753 had very low affinity for the AII-2 receptor ($IC_{50}$ of about $1.4 \times 10^{-4}M$).

The rat adrenal medulla contains a relatively high density of AII receptors which are predominately the AII-2 subtype, as reported in the Chiu et al. paper.

Whitebread et al. (1989) *Biochem. and Biophys. Res. Comm.* 163:284-291, also reports the discovery of two AII receptor subtypes.

Using procedures described by Bennett and Snyder (1976) *J. Biol. Chem.* 254:7423-7430, we have discovered that the rat brain also contains a high density of AII receptors which are predominately the AII-2 subtype. EXP655 displaced the [125I]AII binding in rat brain membranes in a concentration-dependent manner yielding $IC_{50}$ value of $3.2 \times 10^{-7}M$. In contrast, DuP 753 displaced the binding of AII inefficiently, with an $IC_{50}$ value of $1.5 \times 10^{-4}M$.

The distribution of AII-1 and AII-2 receptors in certain regions of the brain was determined by the binding of AII antagonists to different sections of brain slices. The results indicate that there are clusters of DTT-sensitive, DuP 753-sensitive AII binding sites (AII-1 receptors) in the brain; however, the majority of binding sites in the brain are DTT-insensitive and EXP655-sensitive, corresponding to AII-2 receptors.

Despite a high density of AII-2 binding sites in the brain, AII-1 receptor antagonists prevent amnesia induced by renin, as shown by the results in the renin-disrupted passive avoidance retention test described below. These results indicate that AII-1 receptor antagonists, such as the compounds of formula (I), are useful for treatment of CNS disorders, such as learning disorders, cognitive disfunction, schizophrenic polydipsia, centrally induced hypertension, diabetic nephropathy, and excessive milk production. Compound C is the sodium salt of 2-n-propyl-1-[(2'-(1H-tetrazol-5-yl)biphenyl-4-yl)methyl]-4-trifluoromethylimidazole-5-carboxylic acid (Example 265A of EPA 0 324 377). Compound D is the sodium salt of 2-n-propyl-5-hydroxymethyl-1-[(2'-(1H-tetrazol-5-yl)biphenyl-4-yl)methyl]-4-trifluoromethylimidazole (Example 124D of EPA 0 324 377). Both Compounds C and D are AII-1 receptor antagonists.

RENIN-DISRUPTED PASSIVE AVOIDANCE RETENTION

Experimentally naive male Sprague-Dawley rats 100 to 125 days old (Charles River Breeding Laboratories, Kingston, N.Y.), weighing between 175 to 200 gm were used. The animals were housed four per cage ($45.0(L) \times 20.0(H) \times 26.0(W)$ cm) with free access to food and water. They were maintained on a 12 h light-/dark cycle (lights on 600 h) and at a room temperature of $22° \pm 1°$ C. with relative humidity of $50 \pm 10\%$.

The experimental sessions were conducted in a two-compartment passive avoidance box. One compartment, made of clear plastic with a perforated clear plastic floor, measured $21(L) \times 24.5(H) \times 17(W)$ cm and was illuminated with a 60 watt incandescent light bulb placed 36 cm above the floor. The other compartment, made of black plastic, measured $30.5(L) \times 20.3(H) \times 21.5(W)$ cm with a floor made of 4 mm stainless steel rods spaced 1.2 cm apart. A grid floor shocker (Coulbourn Instruments) was connected to the steel rods and provided scrambled footshock. The two compartments were separated by a solenoid-operated slide door (Lafayette Instrument Co., Lafayette, Ind.). An electronic counter (Coulbourn Instruments), triggered by the opening or closing of the slide door, recorded acquisition and retention latencies (latencies were defined as the time it took an animal to enter the dark compartment).

Passive avoidance training began by placing the rat into the clear compartment of the two-compartment passive avoidance box. Following a 10 sec delay, the slide door to the dark compartment was raised. Once the rat moved completely into the dark compartment (all four paws on the shock grid floor) the slide door was lowered, and after a 10 sec delay, a 1.0 mA shock was applied to the grid floor for three sec. A second three sec shock was delivered after an additional 10 sec delay. The rats were immediately removed from the dark compartment and returned to their home cage. A retention test was given 24 h later. It proceeded in the same manner as the training session except that no shock was applied to the grid floor when the rats were provided access to the dark compartment for a maximum of 300 sec.

Renin at 0.1 to 5 µg/5 µL (Sigma Chemicals), and EXP655 at 0.1-100 µg/5 µL were dissolved in 0.85% saline solution. All drugs were administered IVT 60 minutes prior to acquisition training in a volume of 5 µl. Doses are expressed as the free base weight of each compound.

Renin injected IVT produces a reliable memory deficit in rats (Table 1). Two AII-1 receptor antagonists, Compounds C and D, when co-administered with renin protected against the amnesia (Tables 2 and 3). EXP655, an AII-2-specific antagonist, was much less effective in preventing the amnesia (Table 4).

TABLE 1

| Renin-Induced Disruption of Passive Avoidance Retention | |
| --- | --- |
| [renin], (µg/5 µL IVT) | Median Retention Latency (sec) |
| 0 | 300 |
| 0.1 | 254 |
| 0.5 | 117 |
| 1.0 | 27 |
| 3.0 | 56.5 |
| 5.0 | 17 |

TABLE 2

| Compound C Blocks Renin-Induced Disruption of Passive Avoidance Retention | | |
| --- | --- | --- |
| [renin] (µg/5 µL IVT) | [Example 5], (µg/5 µL IVT) | Median Retention Latency, (sec) |
| 0 | 0 | 300 |
| 1.0 | 0 | 48 |
| 1.0 | 10 | 264 |
| 1.0 | 30 | 300 |

TABLE 2-continued

Compound C Blocks
Renin-Induced Disruption
of Passive Avoidance Retention

| [renin] (μg/5 μL IVT) | [Example 5], (μg/5 μL IVT) | Median Retention Latency, (sec) |
|---|---|---|
| 1.0 | 100 | 34.5 |

TABLE 3

Compound C Blocks
Renin-Induced Disruption
of Passive Avoidance Retention

| [renin], (μg/5 μL IVT) | [Example 6], (μg/5 μL IVT) | Median Retention Latency, (sec) |
|---|---|---|
| 0 | 0 | 300 |
| 1.0 | 0 | 32 |
| 1.0 | 30 | 242 |
| 1.0 | 100 | 10 |

TABLE 4

Effects of EXP655 On
Renin-Induced Disruption
of Passive Avoidance Retention

| [renin], (μg/5 μL IVT) | [Example 2], (μg/5 μL IVT) | Median Retention Latency, (sec) |
|---|---|---|
| 0 | 0 | 300 |
| 1.0 | 0 | 15.5 |
| 1.0 | 0.1 | 19 |
| 1.0 | 0.3 | 22 |
| 1.0 | 1.0 | 15 |
| 1.0 | 3.0 | 29 |
| 1.0 | 10 | 15 |
| 1.0 | 30 | 67 |
| 1.0 | 100 | 16 |

DOSAGE FORMS

The compounds of this invention can be administered for the treatment of AII-mediated CNS disorders according to the invention by any means that effects contact of the active ingredient compound with the site of action, i.e., the CNS, in the body of a warm-blooded animal. For example, administration can be parenteral, i.e., subcutaneous, intravenous, intramuscular, or intra peritoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A method of treating impaired cognitive performance which comprises administering to a mammal in need of such treatment an effective amount of a compound having the formula (II):

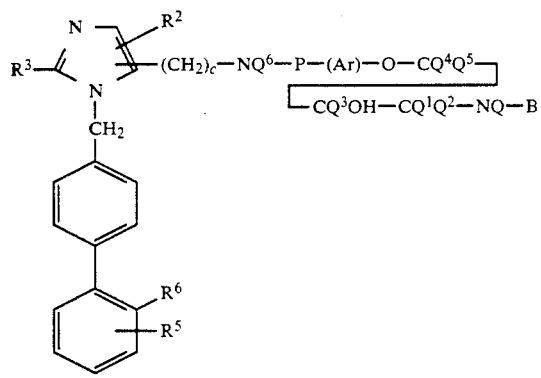

wherein

Q and $Q^1$–$Q^6$, are independently selected from hydrogen and alkyl of 1–4 carbon atoms;

P is a carbonyl group or

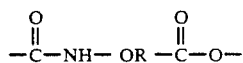

with N and O, respectively, bonded to Ar;

B is an alkyl group of 1 to 6 carbon atoms;

Any of the $-(CH_2)_c-$ groups independently are optionally substituted by one or two alkyl groups of 1 to 4 carbon atoms;

Ar is a benzene ring or a naphthyl or indolyl ring system any of which is optionally substituted in any position by one or more substituents independently selected from alkyl groups of 1 to 4 carbon atoms being optionally substituted by one or more halogen atoms, alkoxy of 1 to 9 carbon atoms, halogen, nitro, amino, carboxy, alkoxycarbonyl of 1 to 4 carbon atoms, and hydroxy;

$R^2$ is H, Cl, Br, or I, alkyl of 1 to 4 carbon atoms, perfluoroalkyl of 1 to 3 carbon atoms, phenyl or $COR^{16}$;

$R^3$ is alkyl, alkenyl or alkynyl of 3 to 7 carbon atoms;

$R^5$ is H, Cl, Br, I, or F, alkyl of 1 to 4 carbon atoms or alkoxy of 1 to 4 carbon atoms;

$R^6$ is $-CO_2H$, $NHSO_2CF_3$ or

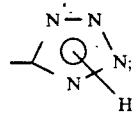

$R^{16}$ is H; alkyl of 1 to 6 carbon atoms; phenyl; phenylalkyl where alkyl is 1 to 6 carbon atoms; OH; alkoxy of 1 to 6 carbon atoms; phenoxy; benzyloxy; $NH_2$; alkylamino or dialkylamino where alkyl is 1 to 6 carbon atoms; or morpholino;

and pharmaceutically acceptable salts thereof.

2. Method of claim 1 wherein the compound of formula (II) is a compound wherein $R^5$ is H, and $R^6$ is $-CO_2H$ or

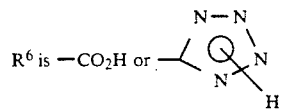

and pharmaceutically acceptable salts thereof.

3. Method of claim 2 wherein the compound is 5-[4-(3-(N-isopropylamino)hydroxypropoxy)indole-2-carboxamidomethyl]-2-n-butyl-1-[(2'-carboxybiphenyl-4-yl)methyl]-4-chloroimidazole.

4. Method of claim 3 wherein the compound is 4-[4-(3-N-isopropylamino)hydroxypropoxy)indole-2-carboxamidomethyl]-2-n-butyl-1-[(2'-(-1H-tetrazol-5-yl)biphenyl-4-yl)methyl]-5-carboxyimidazole.

* * * * *